US010719980B2

(12) United States Patent
Mollus et al.

(10) Patent No.: US 10,719,980 B2
(45) Date of Patent: Jul. 21, 2020

(54) METHOD FOR ANALYZING A TUBE SYSTEM

(75) Inventors: Sabine Mollus, Aachen (DE); Joerg Bredno, San Francisco, CA (US); Juergen Weese, Aachen (DE); Drazenko Babic, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1948 days.

(21) Appl. No.: 12/920,330

(22) PCT Filed: Mar. 2, 2009

(86) PCT No.: PCT/IB2009/050819
§ 371 (c)(1),
(2), (4) Date: Aug. 31, 2010

(87) PCT Pub. No.: WO2009/109887
PCT Pub. Date: Sep. 11, 2009

(65) Prior Publication Data
US 2011/0002517 A1 Jan. 6, 2011

(30) Foreign Application Priority Data
Mar. 6, 2008 (EP) .................................... 08102355

(51) Int. Cl.
*G06T 17/00* (2006.01)
*G06F 19/00* (2018.01)
*G16H 50/50* (2018.01)

(52) U.S. Cl.
CPC .............. *G06T 17/00* (2013.01); *G06F 19/00* (2013.01); *G16H 50/50* (2018.01)

(58) Field of Classification Search
CPC ............... A61K 49/0002; Y10S 977/93; G06F 19/3437; G06F 19/321; A61B 6/032;
(Continued)

(56) References Cited

U.S. PATENT DOCUMENTS

| 4,577,222 A | 3/1986 | Kruger et al. |
| 4,729,379 A | 3/1988 | Ohe |

(Continued)

FOREIGN PATENT DOCUMENTS

| JP | H08126634 A | 5/1996 |
| JP | 20040073578 A | 3/2004 |

(Continued)

OTHER PUBLICATIONS

BruceA. Urban. MD, Lloyd E. Ratner, MD, Elliot K. Fisher, MD,three-Dimensional Volume-render CT Angiography of the Renal Arteries and Veins: Normal Anatomy, Variants and Clinical Applications, Mar. 14, 2000, RadioGraphics, 21,373-386.*

(Continued)

*Primary Examiner* — Victoria P Augustine
*Assistant Examiner* — Teresa S Williams (57) ABSTRACT

A method of analyzing a tube system in particular by image processing of images of the tube system is provided by the present invention. In order to achieve a simulation of a medium flow through a calculated tube model, the present invention gathers a tube model from a specific tube data set. By defining the necessary parameters of a virtual injection of the medium by the user, the medium flows through the model. Using this displayed simulation for generating at least two images leads to an artificial image sequence that might support a person, which wants to examine a real structure, that corresponds to the calculated model. This might be seen in.

21 Claims, 7 Drawing Sheets

(58) Field of Classification Search
CPC ......... A61B 5/026; A61B 6/504; A61B 6/481;
A61B 34/10; A61B 8/06; A61B
2090/374; A61B 6/466; A61B 5/743;
A61B 5/02007; G16H 30/40
USPC ........... 382/128, 130; 703/11; 600/300, 410,
600/419, 431; 381/128, 130; 424/9.3
See application file for complete search history.

(56) References Cited

U.S. PATENT DOCUMENTS

| | | | |
|---|---|---|---|
| 5,222,020 A * | 6/1993 | Takeda | 600/490 |
| 5,296,379 A * | 3/1994 | Gorog et al. | 436/69 |
| 6,521,209 B1 * | 2/2003 | Meade | A61K 49/0002 424/9.3 |
| 6,711,433 B1 | 3/2004 | Geiger et al. | |
| 6,773,263 B2 * | 8/2004 | Nicholls et al. | 434/267 |
| 6,823,204 B2 | 11/2004 | Grass | |
| 7,006,955 B2 * | 2/2006 | Daft et al. | 703/5 |
| 7,050,612 B2 * | 5/2006 | Hale | 382/128 |
| 7,191,110 B1 * | 3/2007 | Charbel | G06F 19/321 703/11 |
| 7,739,090 B2 * | 6/2010 | Charbel et al. | 703/11 |
| 7,787,683 B2 * | 8/2010 | Khamene | G06K 9/00208 382/130 |
| 7,925,330 B2 * | 4/2011 | Kalafut | A61M 5/14546 600/431 |
| 8,000,768 B2 * | 8/2011 | Zhao | A61B 5/055 600/410 |
| 8,010,175 B2 * | 8/2011 | O'Donnell | G06T 7/149 600/407 |
| 8,083,524 B2 * | 12/2011 | Grund-Pedersen | G09B 23/28 434/262 |
| 8,095,382 B2 * | 1/2012 | Boyden et al. | 705/2 |
| 2002/0041654 A1 | 4/2002 | Hayashi | |
| 2002/0168618 A1 * | 11/2002 | Anderson et al. | 434/262 |
| 2004/0082846 A1 | 4/2004 | Johnson | |
| 2007/0053555 A1 | 3/2007 | Ooi et al. | |
| 2007/0103464 A1 | 5/2007 | Kaufman | |
| 2008/0020362 A1 * | 1/2008 | Cotin et al. | 434/267 |
| 2008/0172073 A1 * | 7/2008 | Boyden et al. | 606/155 |
| 2008/0292049 A1 | 11/2008 | Camus | |
| 2008/0294038 A1 | 11/2008 | Weese | |
| 2009/0116715 A1 | 5/2009 | Bredno | |
| 2009/0274358 A1 | 11/2009 | Flohr | |
| 2010/0099991 A1 * | 4/2010 | Snyder | A61B 8/483 600/454 |
| 2010/0113887 A1 * | 5/2010 | Kalafut | A61M 5/007 600/300 |
| 2010/0208971 A1 | 8/2010 | Neukirchen | |
| 2012/0041301 A1 | 2/2012 | Redel | |

FOREIGN PATENT DOCUMENTS

| | | | |
|---|---|---|---|
| WO | 2006073232 A1 | 7/2006 | |
| WO | 2006082558 A2 | 8/2006 | |
| WO | 2006085288 A2 | 8/2006 | |
| WO | 2007066249 A2 | 6/2007 | |
| WO | 2010018500 A1 | 2/2010 | |

OTHER PUBLICATIONS http://www.stanford.edu/~boas/science/IR_plan/index.html; F. Edward Boas, Virtual Angiography, Sep. 26, 2007, select 'Click to rotate' to display 3-D video.*
NPL Google Search—2 pages.*
Dawson et al: "Designing a Computer-Based Simulator for Interventional Cardiology Training"; Catheterization and Cardiovascular Interventions, vol. 51, No. 4, Dec. 2000, pp. 522-527.
Zahlten et al: "Portal Vein Reconstruction Based on Topology"; European Journal of Radiology, vol. 19, 1995, pp. 96-100.
Cebral et al "Qualitative Comparison of Intra-Aneurysmal Flow Structures Determined from Conventional and Virtual Angiograms", Medical Imaging, Proceedings of SPIE, vol. 6511, pp. 6511E-1-6511E-9, 2007.
Sun et al "Quantitative Evaluation of Virtual Angiography for Interventional X-Ray Acquisitions", 2009.
Robert H.P. McGregor, et al., "A Fast Alternative to Computational Fluid Dynamics for High Quality Imaging of Blood Flow", MICCAI 2009, Part I, LNCS 5761, pp. 1224-131, Springer-Verlag Berlin Heidelberg 2009.
J.R. Cebral, et al., "Hemodynamics in Normal Cebral Arteries: Qualitative Compasiron of 4D Phase-Contrast Magnetic Resonance and Image-Based Computational Fluid Dynamics", J. Eng. Math (2009), vol. 64, pp. 367-378.
M.D. Ford, et al., "Virtual Angiography for Visualization and Validation of Computational Models of Aneurysm Hemodynamics", IEEE Transactions on Medical Imaging, vol. 24, No. 12, Dec. 2005, pp. 1586-1592.
J.R. Cebral, et al., "Computational Fluid Dynamics Modeling of Intracranial Aneurysms: Qualitative Comparison with Cebral Angiography", Acad. Radiol. 2007, vol. 14, pp. 804-813.
D.A. Steinman, et al., "Image-Based Computational Simulation of Flow Dynamics in a Giant Intracranial Aneurysm", American Society of Neuroradiology, vol. Apr. 2003, vol. 24, pp. 559-566.
N. Arslan, et al., "CFD Modeling of Blood Flow Inside Human left Coronary Artery Bifurcation with Aneurysms", The European medical and Biological Engineering Conference, Nov. 20-25, 2005, Prague, Czech Republic, pp. 1-7.
J. Svensson, et al., "Feasibility of Patient Specific Aortic Blood Flow CDF Simulation", MICCAI 2006, 4190, Springer-Verlag, Berlin Heidelberg, Germany, 2006, pp. 257-263.
J. Durant, et al., "Toward Quantitative Virtual Angiography Evaluation with in Vitro Studies", IEEE, 2008, pp. 632-635.
H. Schmitt, et al., "Aneurysm Hemodynamics Simulation in 3D-RA", Los Angeles, CA, Apr. 2006, pp. 1-63.
Cusma, Jack T. et al "Digital Subtraction Angiographic Imaging of Coronary Flow Reserve", Circulation, 1987, vol. 75, No. 2, pp. 461-472.
Xu et al "Simulation of Contrast Agent Transport in Arteries with Multilayer Arterial Wall: Impact of Arterial Transmural Transport on the Bolus Delay and Dispersion", Scientific World Journal, vol. 2014, 2014.
Sekiguchi, "Image Processing on Regular Coronary Angiograms for Myocardial Perfusion Measurements", Computers Cardiology, vol. 33, 2006, Pages. pp. 821-824.
Gatta et al, "Towards Robust Myocardial Blush Grade Estimation on Contrast Angiography" Computer Science; vol. 5524 Image Analysis and Processing , 2009 pp. 249-256.
Bredno et al, "Algorithmic Solutions for Live Device-to-Vessel Match", Proceedings of SPIE; vol. 5370; 2004, pp. 1486-1497.
J. Waechter et al., "Model-based blood flow quantification from rotational angiography"; Medical Image Analysis, vol. 12, issue 5, pp. 586-602 (Oct. 2008).
J.R. Linder et al., "Myocardial Perfusion Characteristics and Hemodynamic Profile of MRX-115, a Venous Echocardiographic Contrast Agent, During Acute Myocardial infarction", Journal of the American Society of Echocardiography, Mosby-Year Book, Inc. St. Louis, MO, US, vol. 11, No. 1, Jan. 1, 1998, pp. 36-46.
T. Bolke et al., "Phantom Based Flow Analysis by Means of Dynamic Angiography, CFD and Laser-Doppler-Velocimetry", Nuclear Science Symposium Conference Record, 2007, NSS 2007, IEEE, PI, Oct. 1, 2007, pp. 3440-3445.
Yoganathan et al "Review of Hydrodynamic Principles for the Cardiologist Applications tothe Study of Blood Flow and Jets by Imaging Techniques", J.Am. College of Cardiology, vol. 12, pp. 1344-1353, 1988.
Hawkes, et al "Development of a Model to Predict the Potential Accuracy of Vessel Blood Flow Measurements from Dynamic Antiographic Recordings", Mathematics and Computer Science in Medical Imaging—NATO ASI Series F39 Springer-Verlag, 1988, pp. 469-478.
Hayashi et al New Measurement of Hepatic Blood Flow by Xenon CT System: An Animal Study with PGE1. J. Surg. Res. , vol. 129, pp. 24-30, 2005.

(56) References Cited

OTHER PUBLICATIONS

Kapoor "Techniques of Cardiac Catheterization and Coronary Angiography", Interventional Cardiology, pp. 10-21, 1989.
Van't Hof et al "Angiographic Assessment of Myocardial Reperfusion in Patents treated with Primary Angioplasty for Acute Myocardial Infarction, Myocardial Blush Grade" Circulation, vol. 97, pp. 2302-2306, 1998.
Chen, S. James et al "3-D Reconstruction of Coronary Arterial Tree to Optimize Angiographic Visualization", IEEE Transactions on Medical Imaging, vol. 19, No. 4, Apr. 2000.
Kamiya et al: "Optimal Branching Structure of the Vascular Tree"; Bulletin of Mathematical Biophysics.
PCT/IB2009/050819, ISR and Written Opinion, dated Jun. 18, 2006, 12 Pages.

\* cited by examiner

METHOD FOR ANALYZING A TUBE SYSTEM

FIELD OF THE INVENTION

The present invention relates to the field of analyzing a tubular system, more specifically the invention relates to a method for image processing of a tube system, a respective apparatus and software elements.

BACKGROUND OF THE INVENTION

In many medical procedures, a catheter or other different kind of devices are inserted into tube systems like the arterial system of a patient, and guided to a target location inside the body. This procedure is generally done under imaging guidance using for example a C-arm type of a fluoroscopic apparatus. Periodically, the operating physician takes an X-ray snapshot to see where the tip of the catheter is located or, in the event of difficult manipulations, these are performed by the physician under continuous fluoroscopic imaging.

C-arm based X-ray imaging is the modality of choice for many vascular interventions. In applications such as neuro vascular or hepatovascular treatment, the treatment is often complicated by the complexity of the underlying vascular structures. Due to strong overlap of the often small, tortuous and diseased vessels, angiographic interpretation can be a very laborious task which requires multiple contrast agent injections to visualize the vessel tree from different hierarchy levels. Thereby contrast agents are elements or compounds used to improve the visibility of internal bodily structures in for example an X-ray image.

Further on, it has to be differentiated between interventional imaging, which is applied continuously, with a low dose of radiation and which is for navigation or surveillance and between diagnostic angiography, which uses high doses to improve diagnosis and therapy decisions.

State of the art angiographic imaging relies on two dimensional (2D) sequences and/or on static three dimensional (3D) reconstructions. Although 2D imaging is dynamic, which means that the inflow and the distribution of the injected contrast agent bolus can be surveyed, it is often impossible to resolve the exact vessel topology. 3D imaging overcomes many of these limitations since the vessel tree can be examined from multiple perspectives. But due to the static an often unselective character of the reconstruction assessment of the hemodynamic interrelations is still a challenging task.

SUMMARY OF THE INVENTION

It may be an object of the invention to provide for a fast and efficient method or apparatus for analyzing a tube system.

This object may be realized by the subject-matter according to one of the independent claims. Advantageous embodiments of the present invention are described in the dependent claims.

According to a first exemplary embodiment of the present invention, a method for image processing is presented, the method comprising the following steps: gathering a tube model of a tube tree with at least one tube from a tube data set, selecting a virtual injection point of a medium, simulating a dynamic flow of the medium starting at the virtual injection point, wherein the simulation is generated on basis of flow characteristics wherein the medium flows through the at least one tube of the tube model. The method further on comprises the following steps: using the simulation to generate at least two dynamic images and displaying the dynamic images.

In the following possible further features and advantages of the method according to the first exemplary embodiment will be explained in detail.

The virtual injection point may be a user defined virtual injection point. Therefore the simulation of the dynamic flow may start at the user defined virtual injection point.

The term tube might be used and understood in sense of the terms like vessel, channel, duct, pipe, artery, vein, bronchial tube, or lymph channel. Also a digestive system might be described with the phrases tube system and tube. Any real system comprising a system of different tubes might be investigated with the present combined simulation and display method. Further on, the expression gathering includes the total meaning of the expressions generating, calculating, retrieving, acquiring and computing. Further on, the phrase flow might also include liquid or gaseous flow of matter or flow of heat. Additionally "virtual flow" might be an alternative expression, to describe the simulated medium flow, in order to differentiate the method from real injection situations.

It is believed, that such a method in particular when used for treating patients may reduce the amount of a contrast agent and X-ray exposure in for example the process of angiography. This might be of general benefit for the patient, because less contrast agents mean less stress and fewer possible side effects on the patient. In clinical practice, it is tried to minimize the use of contrast agent. If it is essential for the success of the intervention even large dosages of contrast agent are applied. Afterwards a dialysis is performed to reduce the side effects of the toxic contrast agent.

Analyzing a tube system without having the need to really inject a medium into that tube system might be another advantage of this embodiment of the invention.

Thereby this aspect of the invention is not about providing a diagnosis or about treating patients, but about a solution of the technical problem of analyzing a complex tube system.

All embodiments of the present invention concerning a method, might be carried out with the order of steps as described, nevertheless this has not to be the only and essential order of steps of the method. All different orders and combinations of method steps are herewith described.

As a start a tube model might be extracted from an arbitrary dimensional (one-, two-, three- or four-dimensional) data set using well-known segmentation and modelling techniques. This means that for example a vessel anatomy can be assessed or measured and the measured information might afterwards be stored in a vessel data set. This procedure may describe the phrase of gathering a tube model of a tube tree with at least one tube from the tube data set.

The simulation a flow might further be realized, in part or completely, through different programming languages like Java, C, C++, Mathlab, Labview, PHP or Perl.

By selecting a virtual injection point of a medium, the analyzing person is not forced to use a real injection device. This means that the user chooses for example on a visualizing desktop by mouse clicking, marking or defining coordinates in an arbitrary way, a region in which he wants the simulation to start at. By defining a direction with respect to the virtual injection point, the user constitutes the flow direction of the following flow simulation. This corresponds to the real situation of placing a catheter at a certain point and with a certain orientation.

The selection of a virtual injection point might be user-defined or could also be part of an automatic method, in which the position of a real catheter is extracted from any imaging modality like for example an interventional fluoroscopy. This procedure is called catheter tracking Thereby simulating a dynamic flow of the medium means that the simulation of the flow relies on a calculated and simulated change of the state of the medium within the tube tree. Accordingly, the tube model of a tube tree is considered as a given and fixed volume with its own channels and a physical, numerical simulation regarding a virtual flow of the medium through these channels is performed. Furthermore the method comprises the step that the simulated flow of a virtually injected medium depends and is based on the parent flow of the medium that transports the injected medium in the tube system. This parent flow might for example be a blood flow in arteries or an air flow in bronchial tubes. This inherent simulation of a flow differs clearly from methods, which just paste different pictures together. In contrast to a procedure, where an perfusion image is just overlaid over an image of an computer tomography, which might lead to something like an added but still static flow, this embodiment of the invention leads to a time evolution of the propagating medium. In other words, when having started the simulation, the state of the medium behaves dynamically. Therefore the flow is dynamic.

The tube model might also consist of pathologies such as constricted parts (stenoses) and buldge like sections (aneurysms). Moreover to each model section specific characteristics of the tube's wall such as the modulus of elasticity can be assigned. To make the flow simulation more accurate, fluid-structure interaction (FSI) can be considered which occurs when a fluid interacts with a solid structure.

In other words, in contrast to known visualizations that combine the display of anatomical and functional image data after their respective acquisition, this image processing method provides a prediction of dynamic acquisition before the actual imaging process and without contrast agent usage and X-ray exposure.

In another exemplary embodiment of the invention, a high contrast agent and X-ray burden during acquisitions for diagnosis and therapy is avoided in the following way. First of all, a simulation is performed with the current image geometry and settings. This step might be repeated until the physician is satisfied with the results of the simulation. Not till then, real data, like a real angiography picture, is acquired. This leads to the advantage that the acquisition is successful at the first try and non optimal acquisitions may be avoided.

The change of the visualized flow is, in a first version, based on flow characteristics that are solely extracted from the model's geometry using knowledge from physiology. For example flow fractions might be used in this context. Also material characteristics of the injected material and injector characteristics can be used as a basis for the flow simulation. Further on characteristics of the material, that forms the tube system might be used. In an extension sophisticated methods for flow estimation can be used to extract flow parameters from related data to make the prediction model more accurate. Also the laws of fluid mechanics or thermodynamics might be used to improve the simulation.

Furthermore the injection settings, like the injected volume of a material or the injection pattern, the pulsatility and the flow characteristics of the injected materials might be used to perform and to improve the simulation.

By taking for example two pictures out of this simulated time evolution of the propagating medium and displaying these two dynamic images which dynamic images are linked to the dynamic flow the examining person is provided with an artificial image sequence. This image sequence is displayed on a screen such as a screen of a computed tomography (CT) apparatus, a screen of a CT angiography apparatus (CTA), a screen of a magnetic resonance angiography apparatus (MRA), a screen of a rotational X-ray apparatus, a screen of a ultrasound apparatus (US) or any other screen of an imaging system. Nevertheless the screen might also be a display that is linked to a work-station or a PACS system.

In other words, this embodiment of the present invention offers a person, which is analyzing a tube system or an interesting structure the possibility to assess the flow dynamic interrelations of the system without having the need to use a real injection device like for example a catheter. In contrast to well-known two-dimensional dynamic sequences and static three-dimensional reconstructions, this image processing is able to provide dynamic three-dimensional flow information through an arbitrary tube system. This tube system might be analyzed by for example an examining physician concerning the exact topology and its hemodynamic interrelations.

The method of image processing might for example be applied to simulate airflow through a part of a lung anatomy. The flowing medium in this case would therefore be air. Bolus chase through the digestive system is another alternative application.

In clinical practice the administration of a medium by infusion is done with a well defined bolus. Therefore the simulation of the medium allows a chase of the bolus through the analyzed structure like the digestive system.

But also other technicians who are engaged with tube systems and their flow dynamics like people working with pipeline structures or supply channels for media like for example oil or gas or a mechanical engineer, who is interested in the fuel and exhaust gas flow in the channels of a motor might profit from the image processing method. Further on water and wastewater channel systems in different application fields might be analyzable with this image processing method. In these exemplary embodiments of the invention, different types of databases might be used to deliver data as a tube data set for the gathering of the tube model. For example technical databases of constructing companies, databases of the public administration of wastewater systems or databases of companies running a tube system like oil pipelines might be used for that purpose.

These exemplary embodiments of the present invention all comprise the possibility, to first simulate and optimise an imaging purpose during the simulation, wherein a real acquisition, which might be high in costs and effort, is not done until the optimal situation is reached due to the simulation.

According to another embodiment of the present invention, the method of image processing is for virtual angiography, wherein the tube data set is an angiography data set and wherein the dynamic images are artificial dynamic angiographic images.

Advantages of this virtual angiography might further be an eased angiographic interpretation, hence eased diagnosis and treatment planning, higher workflow efficiency and less contrast agent and fewer X-ray acquisitions and therefore X-ray exposures.

In the case of applying the method to the field of angiography the user first of all may perform an angiogram or an acquisition of a vasculature in three dimensions. This could be done for example by an imaging system like an MR, CT, rotational X-ray or US. In other words any patient specific image might be used for this purpose. Following processes might include segmentation and modelling of the vessel topology using the three-dimensional angiography data, alternatively, a vessel model can be gathered from a respective database. Moreover, data can be extracted from an atlas to build a vessel model. Further on, assigning flow characteristics according to the extracted vessel tree geometry and according to rules known from physiology or physics is a possible step of the method. After having started the simulation of the flow according to the user specified virtual injection point one either follows the Hagen-Poiseuille rules or relyies on more exhaustive computational fluid dynamic simulations. Subsequently the flow simulation is shown starting from the virtual injection point. The at least two dynamic images that are generated out of the simulation are therefore artificial dynamic angiographic images.

In other words, by taking at least two pictures out of the simulation, the examining physician is provided with at least two artificial angiographic images, that show the calculated, virtual time evolution of the propagating medium through the vessel model.

The new virtual angiography feature according to an exemplary embodiment can be integrated in current viewing stations and may ease image interpretation of complex vessel trees for many vascular applications.

The systems and methods according to the above embodiment may be applied to angiographic analysis via a concept called "virtual angiography" or "angio preview". Virtual angiography may combine the advantages of current two dimensional (2D) and three dimensional (3D) imaging since the vessel tree might be presented in 3D, but the visualization is not static. In fact, a virtual contrast bolus will be propagated through a beforehand generated model of the 3D vessel tree. As a prerequisite, for example a vessel model may be extracted from 3D angiographic data set (by e.g. MRA, CTA, CT, US). Starting from a user-defined vessel of interest a dedicated model of for example a contrast agent distribution is propagated through the vessel geometry. The result may be used to generate an artificial angiographic image sequence that may be displayed to the physician. So local and global hemodynamics may easily be assessable. This flow simulation and visualization may be restarted from any (virtual) catheter position so that the respective sub-tree might easily be assessed without further contrast injections.

Another optional step could comprise: labeling of the vessel model for example using registration between the vessel model and a beforehand acquired and labeled volume. Alternatively, the volume can be labeled interactively via a mouse click on a reference vessel, which is by definition the root of the sub tree of interest. For targeted drug delivery the sub tree of interest is the vessel tree that supplies the target treatment region. To the remaining part of the vessel tree the attribute "non-target" is assigned. As mentioned also in the claims, any other attribute can be assigned.

According to another exemplary embodiment, the following steps or procedures can be added to the concept of "virtual angiography" like: mapping a 3D vessel model to an angiographic flow sequence (for example three dimensional Digital Rotational Angiography (3DRA) and two dimensional Digital Substraction Angiography (2D DSA)), extract flow information from the angiographic 2D flow sequence, tune 3D flow simulations with this extracted flow information so that a more individualized flow simulation can be provided.

Furthermore the medium may be a variety or different mixtures of liquids and/or solids such as contrast agents, blood, oil, drugs, microspheres, radioactive substances with different flow characteristics and material properties.

It shall further be noted that beside the step of gathering a tube model, the steps of this and other embodiments of the invention do not necessarily need an interaction with a potential patient.

According to another aspect of the present invention, the method of image processing further comprises the following step: automatically segmenting and modelling of a vessel topology using the angiographic data set and defining a direction with respect to the virtual injection point.

According of another aspect of the invention the step performing a quantitative flow analysis for improving the flow simulation is further comprised.

In the case of a real injection with subsequent flow, this real flow might be analyzed quantitatively, which means that the flowing medium per time unit might be determined. Further parameters like the flow velocity, the pressure or the flow density might be acquired. These acquired data might enable the user to improve a following simulation.

According to another aspect of the present invention, the method further comprises a sub tree visualization for reducing the complexity of the tube tree wherein the sub tree visualization comprises the following steps: selecting a user-defined sub tree of interest by the user, restarting the method of one of the preceding embodiments of the invention, wherein the actual virtual injection point can be different from the preceding virtual injection point.

By providing such a sub tree visualization this embodiment of the present invention enables an examining physician to focus on a special part of the structure, in which he is interested in. Thereby a sub tree in the preceding and in the following is always a sub tree of tubes. This enables an increase of resolution of the flow simulation by focusing on a certain area. Therefore, the physician may give an indication of the sub tree of interest and defines a second or a new virtual injection point for the medium. Then the flow simulation is started and visualized with respect to the virtual injection point.

In a first version, virtual angiography is based on flow characteristics that are solely extracted from the model's geometry using knowledge from physiology. In an extension, sophisticated methods for flow estimation can be used to extract flow parameters from data to make the prediction model more accurate. The data could for example be real time data, data out of an atlas or data that is based on computed fluid dynamics. By defining a new virtual injection point the user refines the simulation in the interested area.

It shall be noted, that the contrary direction of zooming may also be realized in this embodiment of the present invention, in other words, zooming out of a display window. If an image section or sub tree of interest might be too small or if the displayed tree model is too selective, the user might define a new virtual injection point and restart the simulation through a wider section of the tube model as done before. This also comprises alternating sequences of zooming in and zooming out.

Further on, it is important to note that selecting a virtual injection point of a medium as well as selecting a user-defined sub tree of interest is according to the above embodiments of the invention may always be done without using or without having the need to use a real injection device.

Further on, the step of selecting a user-defined sub tree of interest by the user is done by selecting means on a visualizing display or by using an arbitrary work-station. In other words, by mouse clicking, marking or defining coordinates on the surface of an a screen such as a screen of a CT, of a CTA, of a MRA, of a rotational or interventional X-ray apparatus, of US apparatus or any other screen of an imaging system or computing system, the user chooses a new virtual injection point.

According to another exemplary embodiment of the invention, sub tree visualization may be combined with an additional feature that optimizes the viewing angle regarding foreshortening and overlap in the relevant vasculature.

According to another exemplary embodiment of the present invention the following step might be comprised: using different colour maps, where colour represents an additional property of a tube.

Different colours might be useful in order to differentiate for example between the dynamic flow in a target tube tree and a non-target tube tree for targeted delivery of a therapeutic agent. With respect to diagnosis, therapy decisions or supported organ regions the examining physician would prefer to be provided with, a colour-coded visualisation of regions that can be assigned to regions with different properties. This may increase the user friendliness of the present invention.

Further on the option of visualization in form of an overlay of images is possible.

According to another exemplary embodiment of the present invention the following step might be comprised: automatically detecting kissing vessels.

In other words ambiguities concerning the geometry of a vascular tree extracted from image data like for example kissing vessels can be detected automatically.

Thereby kissing vessels are a combination of at least two vessels that feature a junction, where from certain viewing angles it cannot clearly be resolved, whether the vessels really contact each other or whether they cross each other on different heights without any contact.

Kissing vessel configurations may therefore be detected, visualized and resolved in for example a semiautomatic way, for example using a method known from Zahlten et. al., European Journal of Radiology 1995,19,96-100. According to this method, the number of times a centreline voxel is visited during region-growing is counted to detect cycles in the extracted vessel tree topology. Alternatively, flow information like for example the bolus arrival time can be used. To resolve kissing vessel different kinds of visualisations can be exploited like for example the dynamic and flow-oriented visualisation, which is mentioned above. But also static visualisation, which simply shows in colour-coded form the different configurations that are possible to resolve kissing vessels is comprised within this exemplary embodiment of the invention.

Subsequently an illustration of the different flow configurations that are possible for the detected ambiguous configurations is visualized. By providing a user interface to choose for the most likely configuration the semiautomatic way may be provided. After that preferably different colour maps are used to differentiate between flow in a target vessel tree, between flow in a non-target vessel tree and between flow in vessel segments that remain unspecified due to ambiguities like kissing vessels. Speaking generally the visualization of flow information is used to correct and enhance imperfections of the vessel image data set.

According to another exemplary embodiment of the present invention the following step might be comprised computing an optimal viewing angle for the dynamic flow simulation by minimizing at least one of a foreshortening and an overlap of vessels of interest.

At this point the viewing angle is that angle, in which a simulation is shown to the user.

In order to resolve the often complicated underlying vascular structures the virtual angiography or angio preview may calculate that angle for the display of the dynamic flow simulation, at which possible foreshortening or overlap of vessels is minimized.

If two or more vessels seem to conceal parts of each other, the user might not be able to identify clearly how the anatomy of the model really is. Another shortcoming might occur when in inadequate viewing angle is chosen so that many parts of the tube model are distorted due to the chosen perspective.

For subsequent real acquisitions such a viewing angle might be chosen.

Further on, an apparatus for image processing might be another exemplary embodiment of the present invention, wherein the apparatus is arranged to perform the method according to one of the above described embodiments of the invention.

According to another exemplary embodiment of the present invention an apparatus is presented, wherein the apparatus comprises a processor and a user interface, wherein the processor is arranged to retrieve tube data sets and wherein the processor is further arranged to gather a tube model of a tube tree with at least one tube from a tube data set. The user interface is arranged to read in a user selection of a virtual injection point of a medium and a direction with respect to the virtual injection point. The processor is further arranged to simulate a dynamic flow of a medium according to the user defined virtual injection point, wherein a simulation is generated on basis of flow characteristics. Thereby the medium flows through the at least one tube of the tube model. The processor is further arranged to use the simulation to generate at least two dynamic images and to display the images.

As the flow of the medium is simulated, which means computed, it might be an alternative to describe this dynamics as a virtual flow through the tube.

In this apparatus embodiment, which expresses the core apparatus system, only one user interaction is required to define the virtual injection point. Much more user interaction might be required to refine the system for example to define the sub tree of interest, to choose the ingredients to be injected or to resolve ambiguities in the geometry like for example kissing vessels. Most of the needed user interactions of specific cases are hereby included in this embodiment of the apparatus. Further on, the selection of the vessel of interest by the user is done by means of choosing the vessel of interest on a visualizing display or arbitrary screen as described above.

Another additional step might be the definition of the direction of the virtual injection.

In other words, this apparatus is enabled to provide all components to accomplish the method of image processing of the preceding embodiments in order to provide a for example three-dimensional data showing the time evolution of a propagating medium through a tube model with respect to a before defined virtual injection point of the medium.

In case of applying this apparatus to angiography the examining physician is enabled through the apparatus to get a prediction of the flow model of a contrast agent through a vascular structure without having the need to use a real injection device like a catheter in combination with a contrast agent injector. This may lower the physical impact to the patient which is applied through a medical or angiographic examination. Further on, potential costs might be reduced as future contrast agent injections might be avoided through simulating a possible flow by the apparatus.

A workstation may receive the image data from the imaging system or from any kind of image archiving medium. Aspects of the above methods may be realized as software to read out the data, to extract the angiographic information, to generate a 3D vessel model and to simulate blood flow. Output of the software may be virtual angiography resembling and predicting for example the blood flow through a 3D vessel model with respect to a user-defined virtual contrast agent injection point. The workstation may be coupled to interaction devices that allow for user-steered visualization and angiographic analysis. For example the user may input a definition of the VIP, to resolve and/or reroute ambiguous geometries like kissing vessel configurations and change the camera position of the vessel tree visualization.

According to another exemplary embodiment of the present invention the apparatus further comprises an imaging system, wherein the imaging system is arranged to assess a tube anatomy with a tube tree with at least one tube. Further the imaging system is arranged to store information of the assessed tube anatomy in tube data sets, wherein the imaging system is arranged to assess and store a flow data set.

The imaging system is therefore enabled to access for example real perfusion data, that is dynamic, two dimensional medical image data which characterizes the regional blood flow in human tissues. But also an Angiogram might be performed with the imaging system.

It might further be noticed, that instead of using an imaging system also a remote work-station may be comprised in this and every other embodiment of the present invention. Furthermore the required data may stem from different imaging systems.

The imaging system might for example be a CT, a CTA, a MR, a MRA, a rotational or interventional X-ray apparatus, a ultrasound apparatus, a DSA or three dimensional rotational angiography apparatus (3DRA).

Since typically the injection of contrast agents is required an imaging system can be coupled to a contrast agent injection system.

Further on the expressions dynamic flow and dynamic image are used in a sense to differentiate this flow and that image from a procedure, wherein already acquired, different pictures are combined, pasted together or are just overlaid on each other in order to create new "pseudo" dynamic pictures. In contrast to this procedure the dynamic flow simulation and the dynamic images of the embodiments of the present invention represent a gathered tube model, through which tube model a flow of a medium is numerically simulated by calculating the inherent flow parameters of each specific situation. These dynamic images and that dynamic flow simulation are based on flow characteristics, which flow characteristics may be provided through different means.

According to a further embodiment of the present invention, a computer program element is presented, which computer program element is adapted, when in use on a general purposed computer, to cause the computer to perform the steps of a method according to one of the embodiments described above and in the following.

This computer program element might therefore be stored on a computing unit, which might also be part of an embodiment of the present invention. This computing unit may be adapted to perform or induce the performing of the steps of the method described above. Moreover, it may be adapted to operate the components of the above described-apparatus. The computing unit can be adapted to operate automatically and/or to execute the orders of a user. Furthermore, the computing unit can request the selection from a user to process the input from the user.

This embodiment of the invention covers both a computer program, that right from the beginning uses the invention, and a computer program, that by means of an update turns an existing program into a program that uses the invention.

Further on, the computer program element might be able to provide all necessary steps to fullfil the procedure of a virtual angiography as described in the methods and apparatus above.

According to a further embodiment of the present invention, a computer-readable medium is presented wherein the computer-readable medium has a computer program element stored on it, which computer program element is described by the preceding or following sections.

Further on another embodiment of the present invention might be a medium for making a computer program element available for downloading, which computer program element is arranged to perform the method according to one of the above embodiments.

It may be seen as a gist of the invention, that a flow simulation is performed on a tube system which, when e.g. applied to angiography, may allow to perform a virtual angiography without injection of a contrast agent into a patient.

It has to be noted that some of the embodiments of the invention are described with reference to different subject-matters. In particular, some embodiments are described with reference to method type claims whereas other embodiments are described with reference to apparatus type claims. However, a person skilled in the art will gather from the above and the following description that unless other notified in addition to any combination of features belonging to one type of subject-matter also any combination between features relating to different subject-matters is considered to be disclosed with this application.

The aspects defined above and further aspects, features and advantages of the present invention can also be derived from the examples of embodiments to be described hereinafter and are explained with reference to examples of embodiments. The invention will be described in more detail hereinafter with reference to examples of embodiments but to which the invention is not limited.

DETAILED DESCRIPTION OF EMBODIMENTS

Similar or relating components in the several figures are provided with the same reference numerals. The view in the figure is schematic and not fully scaled.

Figure 1:
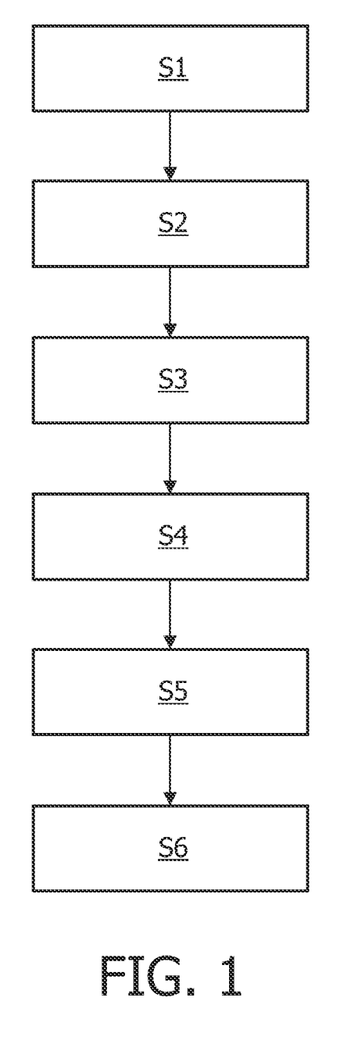
FIG. 1 shows a flow diagram schematically representing a method of image processing according to an embodiment of the present invention.

FIG. 1 shows a possible core method of image processing according to an embodiment of the present invention, wherein this method comprises the following steps: Gathering a tube model of a tube tree with at least one tube from the tube data set S1, selecting a virtual injection point of a medium S2, defining a direction with respect to the virtual injection point S3, simulating a dynamic flow of the medium starting at the user-defined virtual injection point S4, wherein the simulation is generated on basis of flow characteristics, wherein the medium flows through the at least one tube of the tube model using the simulation to generate at least two dynamic images S5 and displaying the dynamic images S6. Thereby the flow simulation might be a three dimensional visualisation.

Figure 1A:
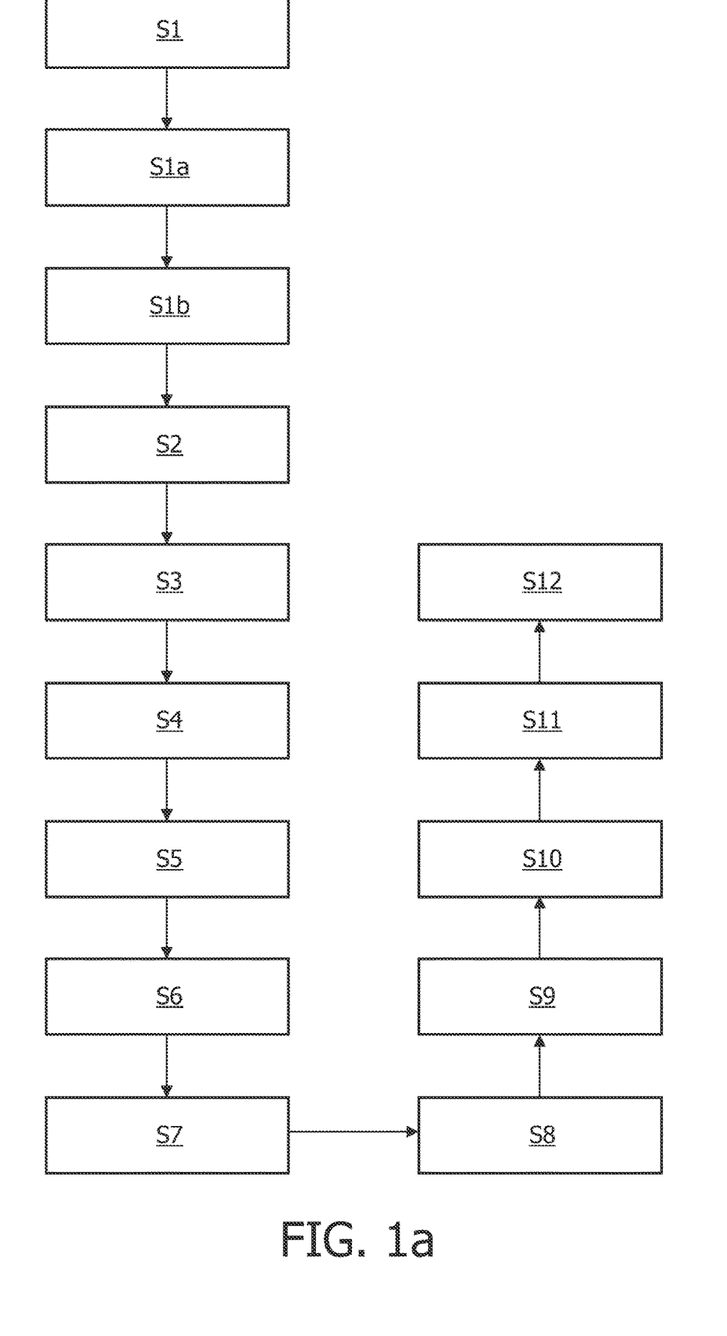
FIG. 1a shows a flow diagram schematically representing a method of image processing according to another embodiment of the present invention.

FIG. 1*a* describes the step of a method of image processing represented in a flow diagram according to an embodiment of the present invention. In the embodiment shown in FIG. 1 by gathering a tube model of a tube tree with at least one tube from a tube data set S1 the basis for the following flow simulation is generated. Thereby the term gathering might include calculating, computing, retrieving, acquiring and generating of a tube model of a tube tree. Further on, the term "tube" might include the expressions vessel, duct, pipe, artery or veins which means that a gathering of a vessel model of a vessel tree with at least one vessel from a vessel data set is possible. As a second step segmentation and modelling techniques might be integrated. Therefore, automatically segmenting and modelling of a vessel topology using the angiographic data set S1*a* may be performed through the method.

If a vessel model is already available, this typically includes a centreline, local radius estimation, and the tree topology, which is the graph of the tree, a topological classification of the vessel centreline voxels in bifurcation, vessel voxel and end points.

Hence, if a vessel model is available, there is no need for further segmentation and/or modelling.

In order to increase a user-friendly performance of the method of image processing a further step, computing an optimal viewing angle for the dynamic flow simulation by minimizing foreshortening and/or overlap of vessels of interest S1*b* may be performed. By a second step, selecting a virtual injection point of a medium S2 a user may be enabled to focus on a part of interest of the vascular structure which he is observing. By defining a direction with respect to the virtual injection point S3 the user constitutes and states the direction of the following simulation direction. By simulating a dynamic flow of the medium starting at the user-defined virtual injection point S4 the method of image processing avoids burdening the patient with additional injection provisions and possible X-ray exposures. Thereby the expression simulating a dynamic flow is used to express the difference of this method step to potential different techniques where for example already acquired pictures of vessels and pictures of a propagating medium are just overlaid on each other or pasted together. Simulating a dynamic flow therefore means that a numerical simulation is calculated through the given and fixed tube structure. This means that the data of the tube model might be interpreted as a fixed volume with its tubes wherein the parameters of a propagating medium are underlying a time evolution. Therefore, the simulation is generated on basis of flow characteristics wherein the medium virtually flows through the at least one tube of the tube model. Further on, the simulation is used to generate at least two dynamic images S5 and is followed by the step displaying the dynamic images S6. Therefore, the examining physician may be provided with an artificial image sequence, which image sequence is a result of the numerical simulation of the virtual flow of the medium.

Furthermore, a sub tree visualization for reducing the complexity of the tube tree S7 might be a further step of the herein described method. Wherein the sub tree visualization comprises the following steps: selecting a user-defined sub tree of interest by the user S8 through which step the user is enabled to focus on a special area of interest. By doing so the user has got the possibility to resolve the area of interested in an improved manner. This selection might just be done by a user interaction like clicking on the display where the tube tree model and the simulation are displayed to the physician. There he may have a comfortable way to choose and select the area of interest.

This may allow for the possibility to simulate dynamically the flow of the potential medium through the new area of interest. The following method step, restarting the method of one of the preceding embodiments S9 wherein the actual virtual injection point can be different from the preceding injection point, may be applied. This is just a description of a convergent process where the user starts a first method of image processing and after having focussed on a special area of interest starting a new virtual angiography in that area. But also the image geometry like for example the viewing angle, the amount of contrast agent and further acquisition parameters might be optimized or determined during this converging process.

In order to differentiate between tubes with respect to diagnosis therapy decision and supported organ region the user is enabled to use different colour maps. Therefore, using different colour maps, where colour represents an additional property of a tube S10 is a possible step of another embodiment of the present invention. This might also be illustrated in the FIG. 2.

A further step might be: automatically detecting kissing vessels or ambiguities of the geometry S11. As these configurations are imperfections of the vessel model, this step might cause to start a new gathering (S1) of a tube model in order to avoid such imperfections in the new model. This describes the situation where crossings or bifurcations of several tubes cannot be resolved clearly and a region of an undefined vessel topology is detected. For example, by using flow information kissing vessels might be resolved. Illustrating the different possible flow configurations to the user is a further step, wherein the user chooses with the user interface the most likely configuration of the possible kissing vessel or ambiguous configuration.

Figure 2:
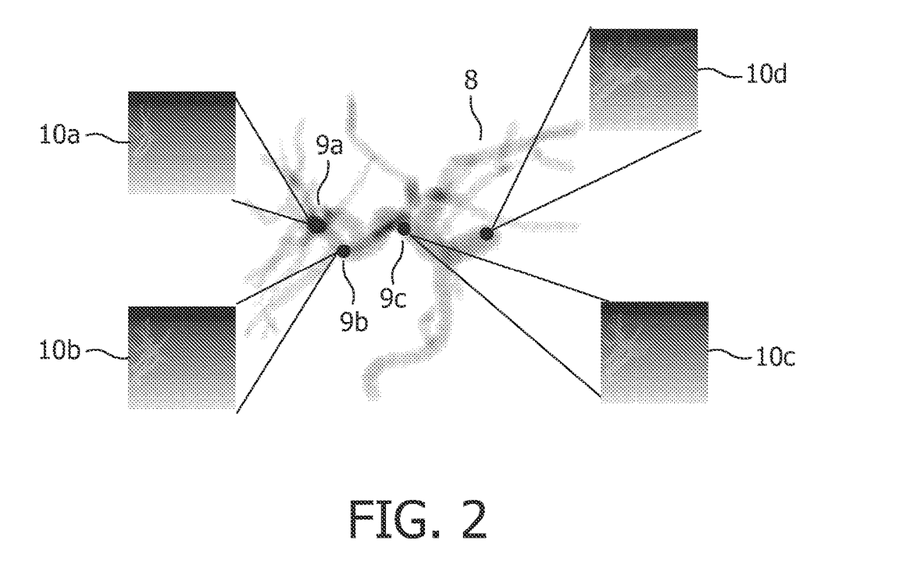
FIG. 2 shows a schematic image of a tube model with different simulated images according to another embodiment of the present invention.

FIG. 2 shows a schematic view of a tube model of a tube tree 8 wherein different virtual injection points 9*a*, 9*b*, 9*c* and 9*d* are indicated. They are represented by the bullets. For each virtual injection point a flow simulation is computed. Here each flow simulation is visualized by a representative image or image sequences 10*a*, 10*b*, 10*c* and 10*d*.

Figure 3:
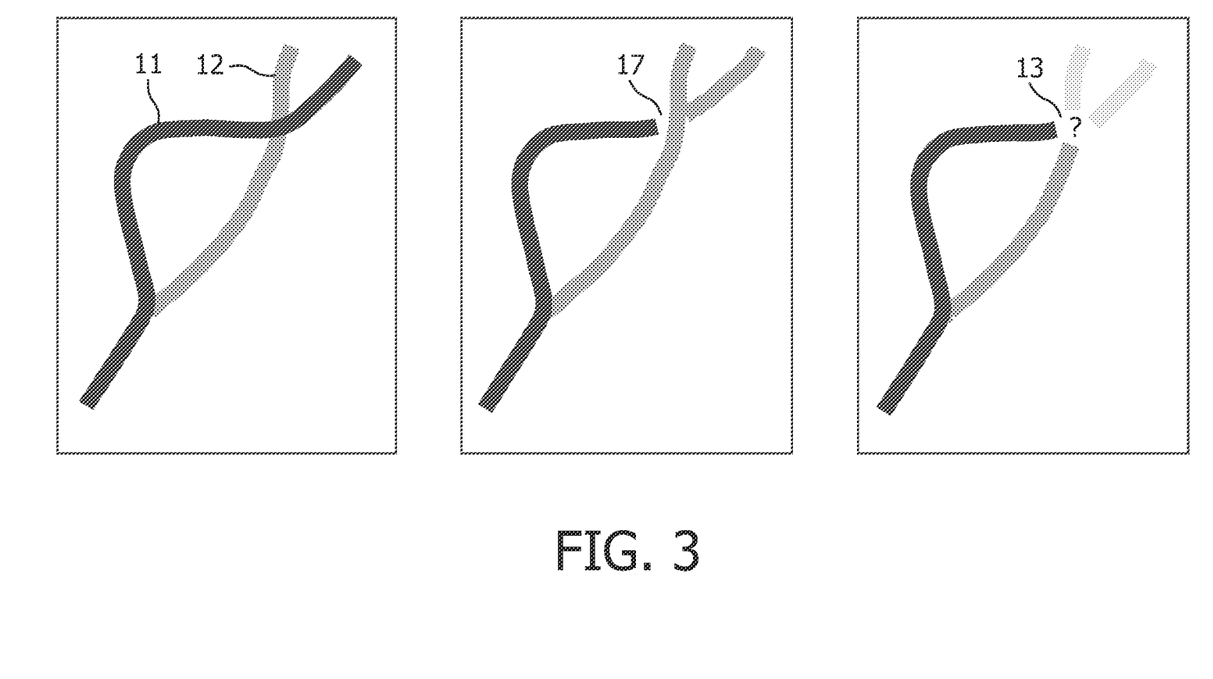
FIG. 3 shows schematically the situation of kissing vessels that might be resolved by an embodiment of the present invention.

FIG. 3 shows a schematic image of a typical vessel ambiguity called kissing vessel configuration, wherein a first tube 11 and a second tube 12 are crossing in this perspective. The part on the right-hand side of FIG. 3 shows the undefined or unresolved section 13, which shall be detected and resolved by an embodiment of the present invention. By means of colour in such images could be visualized for example a non-target vessel; a target vessel, unclear affiliations distal from the kissing vessel location.

The middle part of the three shown pictures in FIG. 3 shows a wrong interpretation 17 of the kissing vessel configuration shown in the left picture. Thereby the part on the right-hand side shows, that the two upper parts of the tubes, shown in bright grey, can not be identified or associated with other parts of tubes shown in black and dark grey.

Figure 4:
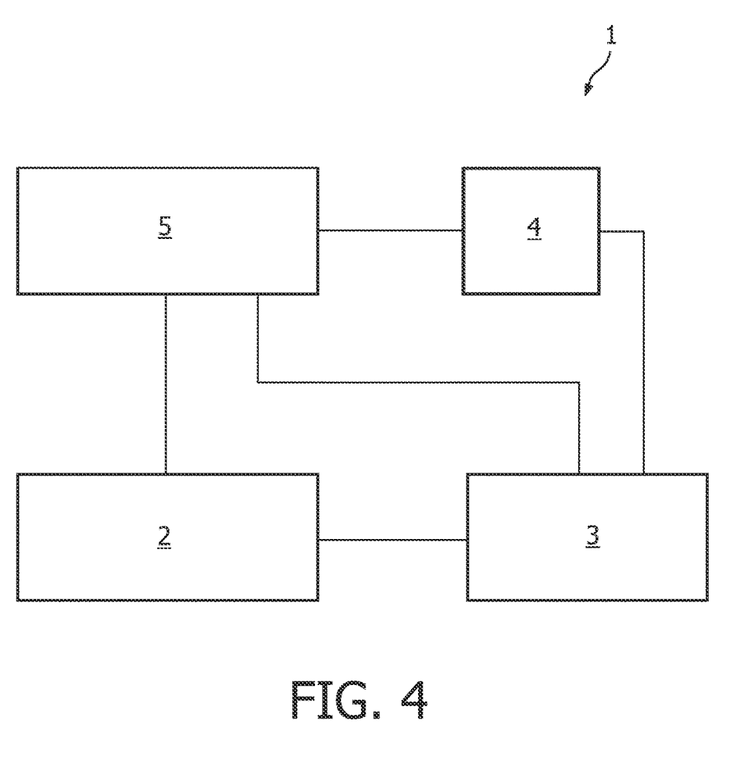
FIG. 4 shows a schematic view of an apparatus according to an embodiment of the present invention.

FIG. 4 shows a schematic view of an apparatus 1 according to an embodiment of the present invention. The apparatus comprises a processor 2, user interface 3, an imaging 4 and a computing unit 5. The different elements are linked together via different connections shown by the different lines. Therefore, the apparatus as an embodiment of the present invention is enabled to control the several elements like the processor or the imaging system to perform the steps of the method according an above embodiment of the invention. This apparatus 1 can therefore provide an examining physician with three-dimensional and dynamical pictures during angiographic analysis, without really injecting a medium into a patient. The already described concept and principle of virtual angiography is therefore completely processable by this apparatus.

Figure 5:
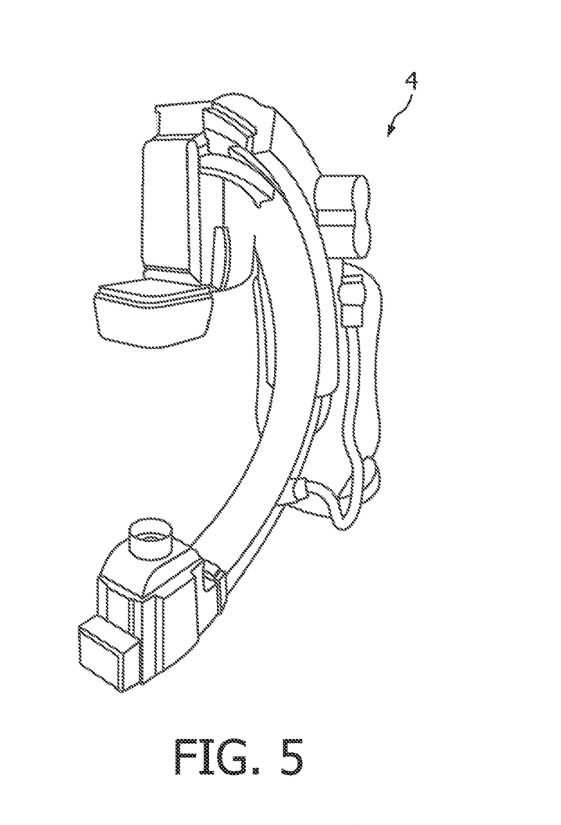
FIGS. 5 and 5a show a further schematic representation of an exemplary imaging system of an apparatus according to another embodiment of the present invention.
Figure 5A:
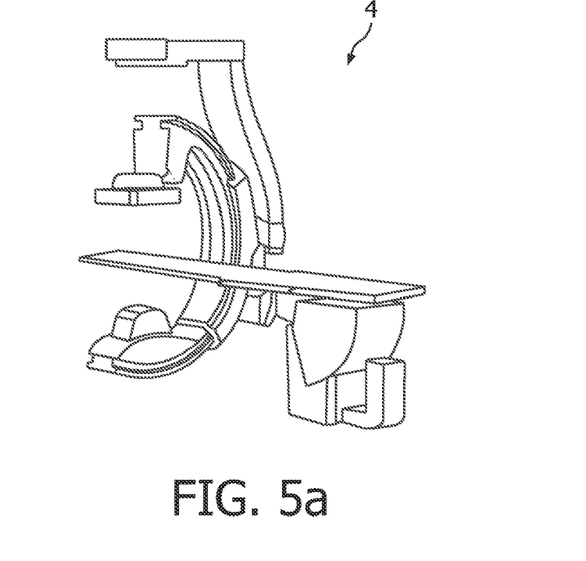

Both FIGS. 5 and 5a show an exemplary embodiment of an imaging system that might be used in the context of virtual angiography as described above and in the following.

Figure 5B:
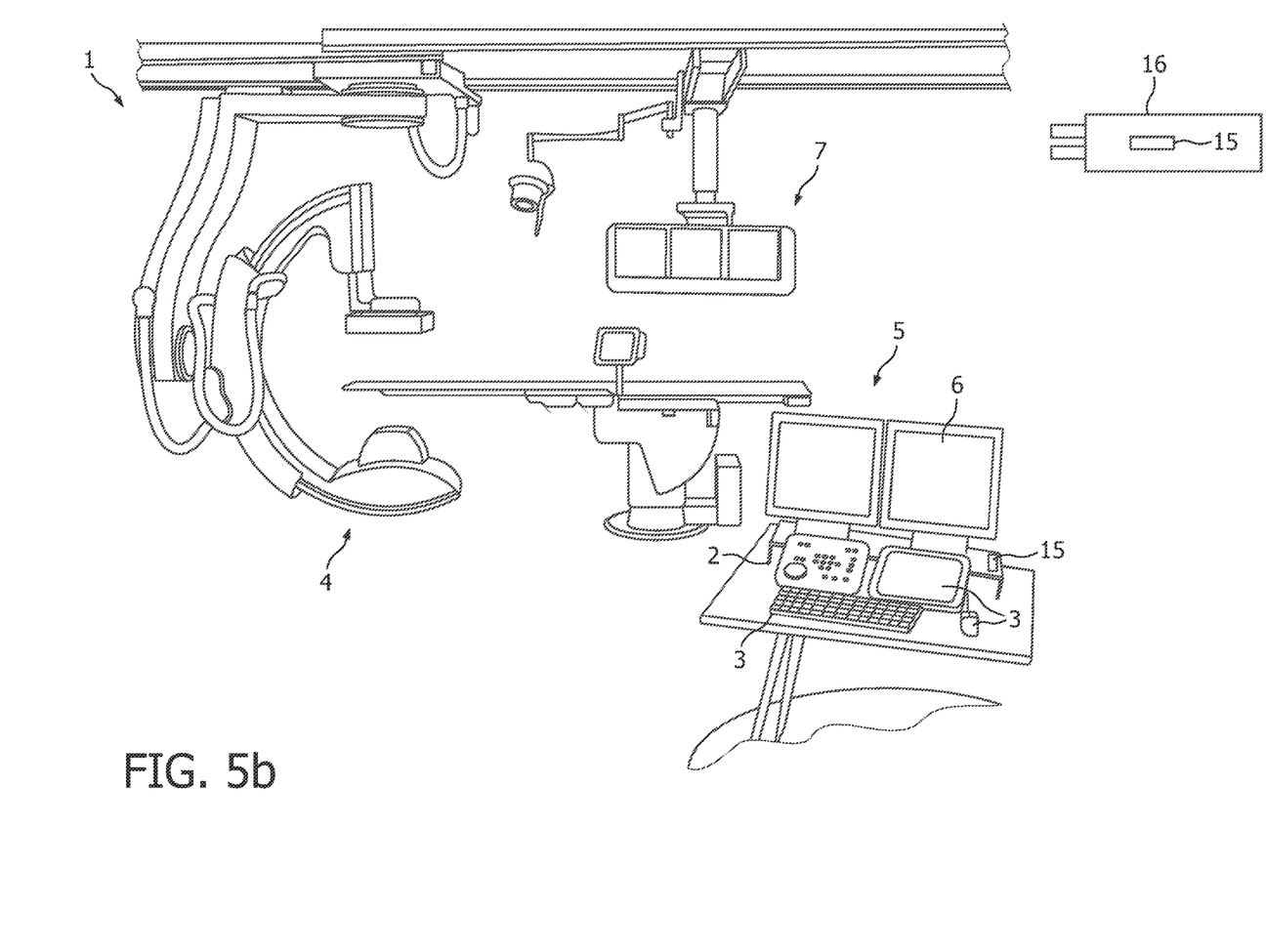
FIG. 5*b* shows a further schematic representation of an apparatus according to another exemplary embodiment of the present invention.

FIG. 5b shows another embodiment of the present invention. On the computing unit 5 may for example be a software installed on, which software may contain a computer program element 15, which is characterized by being adapted when in use on a general purpose computer to cause the computer to perform the steps of the method of image processing that has been described before. A screen 6 or a video system 7 are able to display elements of the embodiment of the present invention like the tube model or the dynamic flow simulation to the user. The computer readable medium 16 might contain such a computer program element 15. Furthermore, an exemplary embodiment of an imaging system 4 is shown.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items or steps recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS

1 Apparatus
2 Processor
3 User interface
4 Imaging system
5 Computing unit
6 Screen
7 Video system
8 Tube model
9, 9a, 9b, 9c, 9d Virtual injection point
10a, 10b, 10c, 10d Computed flow simulation image for respective virtual injection point
11 First tube
12 Second tube
13 Undefined or unresolved section
14 Colour map
15 Computer program element
16 Computer readable medium
17 wrong interpretation of kissing vessel configuration
S1 gathering a tube model of a tube tree with at least one tube from a tube data set
S1a automatically segmenting and modeling of a vessel topology using the angiographic data set
S1b computing an optimal viewing angle for the dynamic flow simulation by minimizing at least one of a foreshortening and a overlap of vessels of interest
S2 selecting a virtual injection point of a medium
S3 defining a direction with respect to the virtual injection point
S4 simulating a dynamic flow of the medium starting at the user defined virtual injection point
S5 using the simulation to generate at least two dynamic images
S6 displaying the dynamic images
S7 sub tree visualization for reducing the complexity of the tube tree
S8 selecting a user defined sub tree of interest by the user
S9 restarting the method of one of the preceding claims
S10 using different colour maps where colour represents an additional property of a tube
S11 automatically detecting kissing vessels
S12 performing a quantitative flow analysis for improving the flow simulation.

The invention claimed is:

1. A simulation device for simulating a real flow through a real tube to determine treatment of a subject, comprising:
a processor configured to extract a tube model of a real tube tree from stored tube data sets including measured information of a real vessel anatomy of the subject including the real tube tree with at least one tube configured to carry a flow of a medium injected into the at least one tube, and a flow data set of flow characteristics of the medium that flows through the at least one tube, said flow data set including one of real time measured data of flow of the medium through the real tube and flow data based on computed fluid dynamics of the flow of the medium through the real tube; and
a display connected to the processor,
wherein the processor is further configured to:
receive from a user interface user selections including a selected point of injection of said medium and a direction of flow of said medium starting from the selected point of injection;
calculate a flow parameter based on the data set of flow characteristics, the selected point of injection and the direction of flow;
generate a simulation of a dynamic flow of a simulated injection of the medium into the selected point of injection to form a simulated flow of the medium starting from the selected point of injection and flowing in the direction through the at least one tube of the tube model based on the flow parameter;

using the simulation, generate at least two dynamic images corresponding to different times during the simulation;

cause the display to display multiple dynamic images from among the at least two generated dynamic images, so as to afford to a viewer an artificial image sequence showing the simulated flow of the medium through the at least one tube of the tube model that models a real tube structure; and determine the treatment of the subject based on the simulation prior to actual imaging of the at least one tube.

2. The device of claim 1, wherein the simulation is generated for virtual angiography, wherein the processor is configured to gather the tube model from said tube data sets, wherein said tube data sets include an angiographic data set, and wherein said generated dynamic images are artificial dynamic angiographic images.

3. The device of claim 2, wherein the processor is configured to automatically segment and model a vessel topology using said angiographic data set and define the direction with respect to the selected point of injection.

4. The device of claim 1, configured for sub tree visualization for reducing complexity of said tube tree, the sub tree visualization comprising, after performing said simulation and said using, and for a user defined, user selected sub tree of interest, performing said simulation, and said using, again such that a current selected point of injection is different from the preceding selected point of injection.

5. The device of claim 1, wherein the processor is configured to cause the display to display different color maps where color represents an additional property of a tube.

6. The device of claim 1, wherein the processor is configured to automatically detect kissing vessels.

7. The device of claim 1, wherein the processor is configured to compute an optimal viewing angle for the dynamic flow simulation by minimizing at least one of a foreshortening and an overlap of vessels of interest.

8. The device of claim 1, wherein said at least two dynamic images correspond to different stages of propagation of said medium through said at least one tube, and wherein said artificial image sequence visually represents the simulated flow of said medium during said simulation.

9. The device of claim 1, wherein said simulated injection is into parent flow, said parent flow being a simulated flow pre-existing at commencement of the simulated injection of the medium at the selected point of injection, the simulation being generated on basis of flow characteristics included in the data set of flow characteristics.

10. The device of claim 1, wherein said simulated injection is from a simulated catheter that, at said selected point of injection, and is in a tube from among said at least one tube.

11. The device of claim 1, wherein said selected point of injection is in a tube from among said at least one tube, and wherein an image from among said at least two dynamic images includes, from among said at least one tube, a tube downstream of said tube in which said selected point of injection is located.

12. The device of claim 1, wherein said processor is configured to automatically, without need for user intervention, execute generation and display of the at least two dynamic images.

13. The device of claim 1, wherein said displaying displays wherein the processor is configured to cause the display to display a video of said multiple ones from among the at least two generated dynamic images.

14. An apparatus for image processing, the apparatus comprising:

a processor configured to extract a tube model of a real tube tree from stored tube data sets including measured information of a real vessel anatomy of a subject including the real tube tree with at least one tube configured to carry a flow of a medium injected into the at least one tube, and a flow data set of flow characteristics of the medium that flows through the at least one tube, said flow data set including one of real time measured data of flow of the medium through the real tube and flow data based on computed fluid dynamics of the flow of the medium through the real tube; and a user interface connected to the processor and configured to read in user selections of selected injection point of a medium and a selected direction with respect to the selected injection point; and a display connected to the processor, wherein the processor is further configured to;

retrieve the tube data sets;

gather the tube model from the tube data sets;

calculate a flow parameter based on the data set of flow characteristics, the selected injection point and the selected direction of flow;

generate a simulation of a dynamic flow to form a simulated flow of the medium starting from the selected injection point and flowing in the selected direction through the at least one tube of the tube model based on the flow parameter;

using the simulation, generate at least two dynamic images corresponding to different times during the simulation;

cause the display to display multiple dynamic images from among the at least two generated dynamic images, so as to afford to a viewer an artificial image sequence showing the simulated flow of the medium through the at least one tube of the tube model that models a real tube structure; and determine treatment of the subject based on the simulation prior to actual imaging of the at least one tube.

15. The apparatus according to claim 14, wherein the apparatus further comprises an imaging system; wherein the imaging system is configured to assess a tube anatomy with a tube tree with at least one tube; wherein the imaging system is configured to store information of the assessed tube anatomy in the tube data sets; and wherein the imaging system is configured to assess and store a flow data set of flow through the tube anatomy.

16. The apparatus of claim 14, the generating being for virtual angiography, said tube data sets including an angiographic data set, and the generated dynamic images are artificial dynamic angiographic images, wherein said apparatus is configured for automatically segmenting and modeling a vessel topology using said angiographic data set.

17. The apparatus of claim 14, wherein the processor is configured to perform a quantitative flow analysis on real flow through a structure described by said tube model, for improving the flow simulation.

18. The apparatus of claim 14, wherein the processor is configured to cause display of different color maps where color represents an additional property of a tube.

19. The apparatus of claim 14, wherein the processor is configured to automatically detect kissing vessels.

20. The apparatus of claim 14, wherein the processor is configured to compute an optimal viewing angle for the dynamic flow simulation by minimizing at least one of a foreshortening and an overlap of selected vessels.

21. The apparatus of claim 14, wherein said at least two dynamic images are to allow a viewer to survey inflow and distribution of an injected contrast agent bolus.

* * * * *